United States Patent
Yoon et al.

(10) Patent No.: US 11,433,054 B2
(45) Date of Patent: Sep. 6, 2022

(54) PHARMACEUTICAL PREPARATION AND PREPARATION METHOD THEREFOR

(71) Applicant: DAEWOONG PHARMACEUTICAL CO., LTD., Hwaseong-si (KR)

(72) Inventors: Jae Hee Yoon, Yongin-si (KR); Han Kang, Yongin-si (KR)

(73) Assignee: DAEWOONG PHARMACEUTICAL CO., LTD., Hwaseong-si (KR)

(*) Notice: Subject to any disclaimer, the term of this patent is extended or adjusted under 35 U.S.C. 154(b) by 85 days.

(21) Appl. No.: 16/626,084

(22) PCT Filed: Jul. 13, 2018

(86) PCT No.: PCT/KR2018/007950
§ 371 (c)(1),
(2) Date: Dec. 23, 2019

(87) PCT Pub. No.: WO2019/013583
PCT Pub. Date: Jan. 17, 2019

(65) Prior Publication Data
US 2020/0206197 A1    Jul. 2, 2020

(30) Foreign Application Priority Data

Jul. 14, 2017 (KR) .................. 10-2017-0089900
Jan. 22, 2018 (KR) .................. 10-2018-0007928

(51) Int. Cl.
| | | |
|---|---|---|
| *A61K 31/426* | (2006.01) | |
| *A61K 9/20* | (2006.01) | |
| *A61K 9/28* | (2006.01) | |
| *A61K 9/50* | (2006.01) | |
| *A61K 47/02* | (2006.01) | |
| *A61K 47/12* | (2006.01) | |
| *A61K 47/34* | (2017.01) | |
| *A61K 47/38* | (2006.01) | |

(52) U.S. Cl.
CPC .......... *A61K 31/426* (2013.01); *A61K 9/2095* (2013.01); *A61K 9/2893* (2013.01); *A61K 9/5089* (2013.01); *A61K 47/02* (2013.01); *A61K 47/12* (2013.01); *A61K 47/34* (2013.01); *A61K 47/38* (2013.01)

(58) Field of Classification Search
CPC .. A61K 31/426; A61K 9/2095; A61K 9/2893; A61K 9/5089; A61K 47/02; A61K 47/12; A61K 47/38
See application file for complete search history.

(56) References Cited

U.S. PATENT DOCUMENTS

2010/0144807 A1* 6/2010 Takaishi ............... A61K 9/2054
514/370
2016/0354328 A1    12/2016 Huang et al.

FOREIGN PATENT DOCUMENTS

| CN | 102170878 A | 8/2011 | |
|---|---|---|---|
| CN | 104288116 A | 1/2015 | |
| CN | 105641706 A | 6/2016 | |
| CN | 106361715 A | 2/2017 | |
| JP | 2016-188181 A | 11/2016 | |
| JP | 2017-048136 A | 3/2017 | |
| KR | 10-2005-0107298 A | 11/2005 | |
| KR | 10-2015-0045500 A | 4/2015 | |
| KR | 10-2016-0117596 A | 10/2016 | |
| KR | 10-2017-0088783 A | 8/2017 | |
| WO | 1999020607 A1 | 4/1999 | |
| WO | 2004041276 A1 | 3/2006 | |
| WO | 2010038690 A1 | 4/2010 | |
| WO | 2012156998 A2 | 11/2012 | |
| WO | WO-2015129893 A1 * | 9/2015 | ........... A61K 31/426 |

OTHER PUBLICATIONS

WO2015/129893 Machine Translation (Year: 2015).*
Xu et al., "Optimization of Mirabegron Sustained-release tables by Central Composite Design-Response Surface Method", Research, 2017, pages , vol. 28, No. 110-114.
State Administration of Traditional Chinese Medicine Professional and Technical Qualification Examination Expert Committee, "Syllabus and detailed rules of the National Traditional Chinese Medicine Professional and Technical Qualification Examination", Nov. 2016, p. 968.
Zhuang, Jianjun et al., "Traditional Chinese Medicine Pharmaceutical Machinery and Pharmaceutical Technology", Nov. 1, 2013, pp. 172-173, ISBN:7509171849.

* cited by examiner

*Primary Examiner* — Sean M Basquill
(74) *Attorney, Agent, or Firm* — Novick, Kim & Lee, PLLC; Jae Youn Kim (57) ABSTRACT

The present invention relates to a pharmaceutical preparation containing an active ingredient and a release-controlling agent for adjusting the release of the active ingredient, in which the active ingredient is at least one selected from among mirabegron and a pharmaceutically acceptable salt thereof, and the release-controlling agent is a hydrogel-forming polymer, the hydrogel-forming polymer being at least one selected from among polyethylene oxide, hydroxypropyl methyl cellulose, hydroxypropyl cellulose, sodium carboxymethylcellulose, and hydroxyethyl cellulose and having an average molecular weight ranging from 100,000 to 8,000,000. The present invention is capable of suppressing the generation of impurities therein and of effectively controlling the release of at least one selected from among mirabegron and a pharmaceutically acceptable salt thereof.

7 Claims, 3 Drawing Sheets

PHARMACEUTICAL PREPARATION AND PREPARATION METHOD THEREFOR

TECHNICAL FIELD

The present invention relates to a pharmaceutical preparation and a method of manufacturing the same, and more particularly to a pharmaceutical preparation, which makes it easy to control the release of mirabegron or a pharmaceutically acceptable salt thereof and the stability of which is attained, and a method of manufacturing the same.

BACKGROUND ART (R)-2-(2-aminothiazol-4-yl)-4'-[2-[(2-hydroxy-2-phenylethyl)amino]ethyl]acetic acid anilide, which was developed by Astellas, has been reported to be a compound having effects of promoting insulin secretion and enhancing insulin sensitivity and anti-obesity and anti-hyperlipidemic effects, and being useful for the treatment of diabetes (International Patent Application Publication No. WO1999/020607).

Also, the above compound has been reported to be useful as a therapeutic agent for urinary urgency, urinary frequency and/or urgent incontinence symptoms that may occur in patients with overactive bladders (International Patent Application Publication No. WO2004/041276).

(R)-2-(2-aminothiazol-4-yl)-4'-[2-[(2-hydroxy-2-phenylethyl)amino]ethyl]acetic acid anilide is commonly referred to as mirabegron, is currently approved for therapy for patients with overactive bladder, and is commercially available as a prolonged-release tablet under the product name Betmiga.

International Patent Application Publication No. WO2010/038690 shows that the elimination half-life of mirabegron is as long as about 18 to 24 hr, and thus, in order to maintain levels thereof in the blood, the need to control the release thereof is not great, but typical immediate-release preparations are influenced by diet and thus the need to develop preparations for avoiding such influence is noted. Moreover, as disclosed in the same document, a preparation capable of sustained drug release of 4 hr or more may reduce the influence of diet, and a preparation using an additive that enables water to penetrate therein and using a hydrogel-forming polymer material is known to correspond thereto (International Patent Application Publication No. WO2010/038690).

The present inventors have come to recognize the need for improvement of such mirabegron preparations during the study thereof.

CITATION LIST

Patent Literature (Patent Document 1) International Patent Application Publication No. WO1999/020607, Specification
(Patent Document 2) International Patent Application Publication No. WO2004/041276, Specification
(Patent Document 3) International Patent Application Publication No. WO2010/038690, Specification

DISCLOSURE

Technical Problem

An objective of the present invention is to provide an improved pharmaceutical preparation.

Another objective of the present invention is to provide a method of manufacturing an improved pharmaceutical preparation.

The objectives of the present invention are not limited to the foregoing, and other objectives not mentioned herein will be clearly understood by those skilled in the art from the following description.

Technical Solution

The present inventors have found that, during the study of mirabegron preparations, impurities may occur, as in the controlled-release pharmaceutical composition disclosed in International Patent Application Publication No. WO2010/038690, and thus conducted research to solve this problem, resulting in the Technical Solution of the present invention.

An embodiment of the present invention provides a pharmaceutical preparation containing an active ingredient and a release-controlling agent for adjusting the release of the active ingredient, the active ingredient being at least one selected from among mirabegron and a pharmaceutically acceptable salt thereof, the release-controlling agent being a hydrogel-forming polymer, and the hydrogel-forming polymer being at least one selected from among polyethylene oxide, hydroxypropyl methyl cellulose, hydroxypropyl cellulose, sodium carboxymethylcellulose and hydroxyethyl cellulose and having an average molecular weight ranging from 100,000 to 8,000,000.

The release-controlling agent may be composed exclusively of the hydrogel-forming polymer.

Also, the release-controlling agent does not contain an additive that enables water to penetrate into the preparation.

The additive that enables water to penetrate into the preparation may be a hydrophilic base.

The hydrophilic base may be at least one selected from the group consisting of polyethylene glycol, polyvinyl pyrrolidone, D-mannitol, D-sorbitol, xylitol, lactose, sucrose, anhydrous maltose, D-fructose, dextran, glucose, polyoxyethylene hardened castor oil, polyoxyethylene polyoxypropylene glycol, polyoxyethylene sorbitan higher fatty acid ester, citric acid, tartaric acid, glycine, β-alanine, lysine hydrochloride and meglumine.

The pharmaceutical preparation may further contain at least one selected from among a binder, an antioxidant, and a lubricant.

The pharmaceutical preparation may be configured such that a coating layer including a coating agent is formed on the surface of a core including the active ingredient, the release-controlling agent, the binder, the antioxidant, and the lubricant.

The coating layer may be formed by dissolving or dispersing the coating agent in a volatile solvent and coating the surface of the core with a film.

The volatile solvent may be ethanol.

The pharmaceutical preparation may include 5 to 25 wt % of the active ingredient, 60 to 90 wt % of the release-controlling agent, 1 to 5 wt % of the binder, 0.1 to 1 wt % of the antioxidant, 1 to 6 wt % of the lubricant, and 1 to 10 wt % of the coating agent.

The lubricant may be composed of silicon dioxide and magnesium stearate, and the amount of silicon dioxide may be 1 to 3 wt % and the amount of magnesium stearate may be 1 to 3 wt % in the pharmaceutical preparation.

The silicon dioxide may be colloidal silicon dioxide.

The coating agent may be a film-coating agent.

The amount of impurities in the pharmaceutical preparation may be 0.2 wt % or less.

The hydrogel-forming polymer may be polyethylene oxide, the average molecular weight thereof ranging from 100,000 to less than 1,000,000.

The hydrogel-forming polymer may be polyethylene oxide, and the polyethylene oxide may include polyethylene oxide having an average molecular weight ranging from 100,000 to less than 500,000 and polyethylene oxide having an average molecular weight ranging from 500,000 to less than 1,000,000.

Based on 100 parts by weight of polyethylene oxide having an average molecular weight ranging from 100,000 to less than 500,000, the amount of polyethylene oxide having an average molecular weight ranging from 500,000 to less than 1,000,000 may be, but is not limited to, for example, 10 to 1000 parts by weight, preferably 50 to 500 parts by weight, more preferably 100 to 350 parts by weight, and even more preferably 250 to 350 parts by weight.

The pharmaceutical preparation may be an oral preparation.

The amount of the active ingredient may be 1 to 500 mg.

The pharmaceutical preparation may be administered once a day.

Another embodiment of the present invention provides a method of manufacturing a pharmaceutical preparation, the method including (A) manufacturing granules by dispersing or dissolving a binder and an antioxidant in a solvent to afford a solution, which is then mixed with a mixture of an active ingredient and a release-controlling agent and (B) obtaining a tablet by adding the granules with a lubricant and performing tableting, in which the binder is hydroxypropyl cellulose, the antioxidant is butylhydroxytoluene, the active ingredient is at least one selected from among mirabegron and a pharmaceutically acceptable salt thereof, the release-controlling agent is a hydrogel-forming polymer, the hydrogel-forming polymer is at least one selected from among polyethylene oxide, hydroxypropyl methyl cellulose, hydroxypropyl cellulose, sodium carboxymethylcellulose and hydroxyethyl cellulose, the average molecular weight thereof ranging from 100,000 to 8,000,000, and the lubricant is silicon dioxide and magnesium stearate.

The method of manufacturing the pharmaceutical preparation may further include (C) coating the tablet with a film by dissolving or dispersing a film-coating agent in a volatile solvent.

The volatile solvent may be ethanol.

Advantageous Effects

According to the present invention, the preparation is capable of inhibiting the generation of impurities therein and of effectively controlling the release of at least one selected from among mirabegron and a pharmaceutically acceptable salt thereof.

MODE FOR INVENTION

Hereinafter, the advantages and features of the present invention will be more clearly understood from the following detailed description taken in conjunction with the accompanying drawings. However, the present invention is not limited to the embodiments disclosed herein, and may be modified into different forms. These embodiments are provided to thoroughly explain the disclosure and to sufficiently transfer the spirit of the present invention to those skilled in the art, and the present invention is merely defined by the scope of the claims.

An embodiment of the present invention pertains to a pharmaceutical preparation containing an active ingredient and a release-controlling agent for adjusting the release of the active ingredient.

The active ingredient is at least one selected from among mirabegron and a pharmaceutically acceptable salt thereof.

Mirabegron has a compound name of (R)-2-(2-aminothiazol-4-yl)-4'-[2-[(2-hydroxy-2-phenylethyl)amino]ethyl] acetic acid anilide, and may be represented by the following structural formula.

Examples of the pharmaceutically acceptable salt of mirabegron may include, but are not limited to, acid addition salts with inorganic acids such as hydrochloric acid, hydrobromic acid, hydroiodic acid, sulfuric acid, nitric acid, phosphoric acid, etc., and acid addition salts with formic acid, acetic acid, propionic acid, oxalic acid, malonic acid, succinic acid, fumaric acid, maleic acid, lactic acid, malic acid, citric acid, tartaric acid, carbonic acid, picric acid, methanesulfonic acid, ethanesulfonic acid, glutamic acid and the like.

The dose of the active ingredient may be appropriately determined depending on individual conditions in consideration of the symptoms, the administration subject's age and gender, and the like, and in the case of typical oral administration to adults, the active ingredient may be administered once a day at a dose of 0.01 mg/kg to 100 mg/kg.

In an embodiment of the present invention, the preparation may be used for oral administration. Also, it may be administered once a day.

The active ingredient is preferably contained in an amount of 5 to 28 wt %, and more preferably 5 to 25 wt %, based on the total weight of the pharmaceutical preparation. Within the above range, the release thereof may be more easily controlled. The pharmaceutical preparation is provided in a unit dosage form, and the amount of the active ingredient in a unit dosage form is preferably 1 to 500 mg, and more preferably 10 to 300 mg.

The release-controlling agent is meant to include a release-delaying agent that delays the release of the active ingredient from the preparation. The release-controlling agent is a hydrogel-forming polymer. The hydrogel-forming polymer is a polymer that swells upon contact with a water-soluble medium, and is at least one selected from among polyethylene oxide, hydroxypropyl methyl cellulose, hydroxypropyl cellulose, sodium carboxymethylcellulose and hydroxyethyl cellulose, and the average molecular weight thereof falls in the range of 100,000 to 8,000,000, and preferably 100,000 to less than 1,000,000. Preferably, the hydrogel-forming polymer is polyethylene oxide. The polyethylene oxide may include polyethylene oxide having an average molecular weight ranging from 100,000 to less than 500,000 and polyethylene oxide having an average molecular weight of 500,000 to less than 1,000,000. Here, based on 100 parts by weight of the polyethylene oxide having an average molecular weight ranging from 100,000 to less than 500,000, the amount of the polyethylene oxide having an average molecular weight of 500,000 to less than 1,000,000 may be, but is not limited to, for example, 10 to 1000 parts by weight, preferably 50 to 500 parts by weight, more preferably 100 to 350 parts by weight, and even more preferably 250 to 350 parts by weight. When such a polymer is applied in this way, controlled release may become easier. The average molecular weight may be a number average molecular weight or a weight average molecular weight. The release-controlling agent is composed exclusively of the hydrogel-forming polymer. In particular, the release-controlling agent does not include an additive that enables water to penetrate into the preparation. The additive that enables water to penetrate into the preparation may be a hydrophilic base. The hydrophilic base is known to be typically used in the mirabegron preparation, and the amount of water necessary to dissolve 1 g of the hydrophilic base may be 10 mL or less in an embodiment, 6 mL or less in another embodiment, 5 mL or less in still another embodiment, and 4 mL or less in yet another embodiment, at 20±5° C. The hydrophilic base may be at least one selected from the group consisting of, for example, polyethylene glycol, polyvinyl pyrrolidone, D-mannitol, D-sorbitol, xylitol, lactose, sucrose, anhydrous maltose, D-fructose, dextran, glucose, polyoxyethylene hardened castor oil, polyoxyethylene polyoxypropylene glycol, polyoxyethylene sorbitan higher fatty acid ester, citric acid, tartaric acid, glycine, β-alanine, lysine hydrochloride and meglumine. Since such a hydrophilic base is not used, it appears that the generation of impurities may be suppressed, as is confirmed later.

The release-controlling agent is preferably contained in an amount of 60 to 90 wt % based on the total weight of the pharmaceutical preparation. When the amount thereof falls out of the above range, there is the concern that it will not be easy to control the release of the active ingredient.

In an embodiment of the present invention, the pharmaceutical preparation may further include at least one selected from among a binder, an antioxidant, and a lubricant.

The binder is not limited to, but may be at least one selected from among, for example, hydroxypropyl cellulose, hydroxypropyl methyl cellulose, polyvinyl pyrrolidone, methyl cellulose, carboxymethyl cellulose, sodium carboxymethylcellulose, trehalose, and pullulan, and is preferably hydroxypropyl cellulose. The amount of the binder is preferably 1 to 5 wt % based on the total weight of the pharmaceutical preparation.

The antioxidant is not limited to, but may be at least one selected from among, for example, butylhydroxytoluene (BHT), propyl gallate (PG), butylhydroxyanisole (BHA), ascorbic acid, sodium ascorbate, erythorbic acid, sodium nitrite, sodium bisulfite, sodium pyrosulfite, citric acid and sodium edetate, and is preferably butylhydroxytoluene (BHT).

The amount of the antioxidant is preferably 0.1 to 1 wt % based on the total weight of the pharmaceutical preparation.

The lubricant is not limited to, but may be at least one selected from among, for example, magnesium stearate, calcium stearate, silicon dioxide, and talc. The amount of the lubricant is preferably 1 to 6 wt %, and more preferably 2 to 6 wt %, based on the total weight of the pharmaceutical preparation. The lubricant is preferably composed of silicon dioxide and magnesium stearate. In the pharmaceutical preparation, the amount of silicon dioxide is preferably 0.5 to 3 wt %, and more preferably 1 to 3 wt %, and the amount of magnesium stearate is preferably 0.5 to 3 wt %, and more preferably 1 to 3 wt %. Here, the silicon dioxide may be colloidal silicon dioxide.

In an embodiment of the present invention, the pharmaceutical preparation may be an oral preparation.

When the pharmaceutical preparation of the present invention includes all of the binder, the antioxidant and the lubricant, it may be provided in the form of a tablet containing the active ingredient, the release-controlling agent, the binder, the antioxidant, and the lubricant.

In an embodiment of the present invention, the pharmaceutical preparation may include, based on the total weight thereof, 5 to 28 wt % of the active ingredient, 60 to 90 wt % of the release-controlling agent, 1 to 5 wt % of the binder, 0.1 to 1 wt % of the antioxidant, and 1 to 6 wt % of the lubricant. When the amounts thereof fall out of the above ranges, there is the concern that it will not be easy to control the release of the active ingredient.

Also, the pharmaceutical preparation according to an embodiment of the present invention may be configured such that a coating layer including a coating agent may be formed on the surface of a core including the active ingredient, the release-controlling agent, the binder, the antioxidant, and the lubricant. Such a coating layer may be formed by dissolving or dispersing the coating agent in a volatile solvent and coating the surface of the core with a film. When the coating layer is formed through film coating using the volatile solvent, a more stable tablet may be obtained, and the generation of impurities may be further suppressed. Here, the volatile solvent is not limited, so long as it is capable of dissolving or dispersing the film-coating agent and is volatile, and may be, for example, ethanol. Here, the pharmaceutical preparation may be provided in the form of a coated tablet. The pharmaceutical preparation according to an embodiment of the present invention may include, based on the total weight thereof, 5 to 25 wt % of the active ingredient, 60 to 90 wt % of the release-controlling agent, 1 to 5 wt % of the binder, 0.1 to 1 wt % of the antioxidant, 1 to 6 wt % of the lubricant, and 1 to 10 wt % of the coating agent. When the amounts thereof fall out of the above ranges, there is the concern that it will not be easy to control the release of the active ingredient.

The lubricant is composed of silicon dioxide and magnesium stearate, and in the pharmaceutical preparation, the amount of silicon dioxide is preferably 0.5 to 3 wt %, and more preferably 1 to 3 wt %, and the amount of magnesium stearate is preferably 0.5 to 3 wt %, and more preferably 1 to 3 wt %.

The coating agent may be a film-coating agent. The film-coating agent is not limited, so long as it is able to coat the surface of the pharmaceutical preparation, but may include, for example, an Opadry film-coating agent.

An Opadry (registered trademark) film-coating agent (available from Colorcon Inc.) is a 1-step film-coating system, in which a polymer, a plasticizer and a pigment, as necessary, may be combined in an anhydrous concentrate.

In an embodiment of the present invention, the amount of impurities may be 0.2 wt % or less based on the total weight of the pharmaceutical preparation. The impurities are other individual related substances. The other individual related substances indicate related substances, except (R)-2-((4-aminophenethyl)amino)-1-phenylethanol, 2-(2-aminothiazol-4-yl)-N-(4-(2(phenethylamino)ethyl)phenyl)acetamide, (R)-2-(2-aminothiazol-4-yl)-N-(4-(2-((4-(2-((2-hydroxy-2-phenylethyl)amino)ethyl)phenyl)amino)-2- oxoethyl)thiazol-2-yl)acetamide, and (R)-2-(2-aminothiazol-4-yl)-N-(4-(2-(2-aminothiazol-4-yl) acetamido)phenethyl)-N-(2-hydroxy-2-phenylethyl) acetamide, among total related substances. As described above, the pharmaceutical preparation of the present invention is a preparation having stability in which the generation of impurities is drastically suppressed to the level of 0.2 wt % or less, which will be confirmed through the following experimental examples. When using a hydrophilic base as in the controlled-release pharmaceutical composition disclosed in International Patent Application Publication No. WO2010/038690, the amount of impurities exceeds 0.2 wt %, based on which the present invention is regarded as superior.

Figure 1:
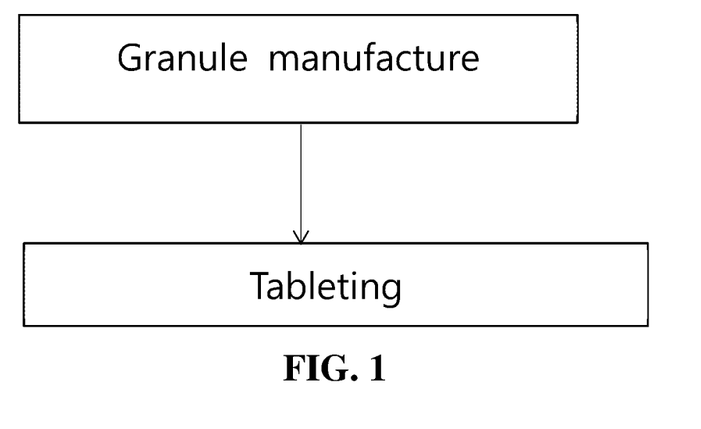
FIG. 1 is a flowchart showing a process of manufacturing a pharmaceutical preparation according to an embodiment of the present invention.

Below is a detailed description of the method of manufacturing the pharmaceutical preparation according to an embodiment of the present invention with reference to FIG. 1. FIG. 1 is a flowchart showing the process of manufacturing the pharmaceutical preparation according to an embodiment of the present invention.

In an embodiment of the present invention, the method of manufacturing the pharmaceutical preparation may include, as shown in FIG. 1, (A) manufacturing granules and (B) obtaining a tablet. In step (A), a binder and an antioxidant are dispersed or dissolved in a solvent, and are then mixed with a mixture of an active ingredient and a release-controlling agent, thereby manufacturing granules. In step (B), the granules are added with a lubricant and tableted, thus obtaining a tablet. Here, the binder is hydroxypropyl cellulose, the antioxidant is butylhydroxytoluene, the active ingredient is at least one selected from among mirabegron and a pharmaceutically acceptable salt thereof, the release-controlling agent is a hydrogel-forming polymer, the hydrogel-forming polymer being at least one selected from among polyethylene oxide, hydroxypropyl methyl cellulose, hydroxypropyl cellulose, sodium carboxymethylcellulose and hydroxyethyl cellulose and having an average molecular weight ranging from 100,000 to 8,000,000, and the lubricant is silicon dioxide and magnesium stearate. Thereby, the pharmaceutical preparation may be effectively obtained in the form of a tablet.

The method of the present invention may further include (C) coating the tablet with a film by dissolving or dispersing a film-coating agent in a volatile solvent. When film coating is performed using the volatile solvent in this way, greater stability of the tablet may be attained and the generation of impurities may be further suppressed, which is confirmed based on the experimental results. Compared to when water is used as a solvent, as in the controlled-release pharmaceutical composition disclosed in International Patent Application Publication No. WO2010/038690, the use of the volatile solvent is able to reduce the water content of the preparation, whereby the generation of impurities such as related substances may be further suppressed. The volatile solvent is not limited, so long as it is able to dissolve or disperse the film-coating agent and is volatile, but may be, for example, ethanol.

In addition thereto, the preparation of the present invention may be manufactured through appropriate methods known in the art, and reference may be made to, for example, Remington's Pharmaceutical Science (latest edition), Mack Publishing Company, Easton Pa., etc.

Although common descriptions are omitted in order to avoid undue redundancy, the matters described in connection with the pharmaceutical preparation and the method of manufacturing the same according to the present invention are applied equally to each other in the same scope unless they are contradictory to each other.

A better understanding of the present invention is given through the following examples, comparative examples and experimental examples. The materials used in the following examples, comparative example, and experimental examples corresponded to the best commercially available grades.

<Examples 1 to 5> Coated Tablet

Example 1

75 g of mirabegron and 225 g of polyethylene oxide (made by Dow Chemical, WSR N-80, having an average molecular weight of 200,000) were mixed, placed in a high-speed mixer, added with a solution of hydroxypropyl cellulose (made by Nippon Soda, HPC-L, hereinafter the same) and butylhydroxytoluene (made by Spectrum Chemical, hereinafter the same) dissolved in ethanol, mixed and granulated, thus obtaining granules. The granules thus obtained were dried, screened, mixed with 7.5 g of pulverized magnesium stearate (made by FACI, hereinafter the same) and 7.5 g of light anhydrous silicic acid (made by Fuji Silysia, Aerosil 200, colloidal silicon dioxide, hereinafter the same), and tableted using a rotary tableting machine, thus obtaining a tablet (216 mg per tablet). Using a coating machine, the tablet thus obtained was spray-coated with a dispersion solution of a film-coating agent (Opadry; Opadry 03F220071_Yellow (containing HPMC 60P, yellow iron oxide, and PEG8000), hereinafter the same) in ethanol, thereby yielding a pharmaceutical preparation (coated tablet, 224 mg per tablet).

Example 2

75 g of mirabegron and 225 g of polyethylene oxide (made by Dow Chemical, WSR-1105, having an average molecular weight of 900,000) were mixed, placed in a high-speed mixer, added with a solution of hydroxypropyl cellulose and butylhydroxytoluene dissolved in ethanol, mixed, and granulated, thus obtaining granules. The granules thus obtained were dried, screened, mixed with 7.5 g of pulverized magnesium stearate and 7.5 g of light anhydrous silicic acid, and tableted using a rotary tableting machine, thus obtaining a tablet (216 mg per tablet). Using a coating machine, the tablet thus obtained was spray-coated with a dispersion solution of a film-coating agent (Opadry) in ethanol, thereby yielding a pharmaceutical preparation (coated tablet, 224 mg per tablet).

Example 3

75 g of mirabegron, 112.5 g of polyethylene oxide WSR N-80 and 112.5 g of polyethylene oxide WSR-1105 were mixed, placed in a high-speed mixer, added with a solution of hydroxypropyl cellulose and butylhydroxytoluene dissolved in ethanol, mixed, and granulated, thus obtaining granules. The granules thus obtained were dried, screened, mixed with 7.5 g of pulverized magnesium stearate and 7.5 g of light anhydrous silicic acid, and tableted using a rotary tableting machine, thus obtaining a tablet (216 mg per tablet). Using a coating machine, the tablet thus obtained was spray-coated with a dispersion solution of a film-coating agent (Opadry) in ethanol, thereby yielding a pharmaceutical preparation (coated tablet, 224 mg per tablet).

Example 4

75 g of mirabegron, 101.25 g of polyethylene oxide WSR N-80 and 123.75 g of polyethylene oxide WSR-1105 were mixed, placed in a high-speed mixer, added with a solution of hydroxypropyl cellulose and butylhydroxytoluene dissolved in ethanol, mixed, and granulated, thus obtaining granules. The granules thus obtained were dried, screened, mixed with 7.5 g of pulverized magnesium stearate and 7.5 g of light anhydrous silicic acid, and tableted using a rotary tableting machine, thus obtaining a tablet (216 mg per tablet). Using a coating machine, the tablet thus obtained was spray-coated with a dispersion solution of a film-coating agent (Opadry) in ethanol, thereby yielding a pharmaceutical preparation (coated tablet, 224 mg per tablet).

Example 5

75 g of mirabegron, 56.25 g of polyethylene oxide WSR N-80 and 168.75 g of polyethylene oxide WSR-1105 were mixed, placed in a high-speed mixer, added with a solution of hydroxypropyl cellulose and butylhydroxytoluene dissolved in ethanol, mixed and granulated, thus obtaining granules. The granules thus obtained were dried, screened, mixed with 7.5 g of pulverized magnesium stearate and 7.5 g of light anhydrous silicic acid, and tableted using a rotary tableting machine, thus obtaining a tablet (216 mg per tablet). Using a coating machine, the tablet thus obtained was spray-coated with a dispersion solution of a film-coating agent in ethanol, thereby yielding a pharmaceutical preparation (coated tablet, 224 mg per tablet).

Respective recipes of Examples 1 to 5 are shown in Table 1 below.

TABLE 1

| Example | Example 1 | Example 2 | Example 3 | Example 4 | Example 5 |
|---|---|---|---|---|---|
| Mirabegron (g) | 75 | 75 | 75 | 75 | 75 |
| Polyethylene oxide (WSR N-80, g) | 225 | — | 112.5 | 101.25 | 56.25 |
| Polyethylene oxide (WSR-1105, g) | — | 225 | 112.5 | 123.75 | 168.75 |
| HPC-L (g) | 7.5 | 7.5 | 7.5 | 7.5 | 7.5 |
| Butylhydroxytoluene (g) | 1.5 | 1.5 | 1.5 | 1.5 | 1.5 |
| Magnesium stearate (g) | 7.5 | 7.5 | 7.5 | 7.5 | 7.5 |
| Aerosil 200 (g) | 7.5 | 7.5 | 7.5 | 7.5 | 7.5 |
| Film-coating agent (g) | Appropriate amount | Appropriate amount | Appropriate amount | Appropriate amount | Appropriate amount |

<Comparative Examples 1 to 5> Coated Tablet

The preparations of Comparative Examples 1 to 5 were manufactured using both an additive that enables water to penetrate into the preparation and a hydrogel-forming polymer, in the same manner as described in International Patent Application Publication No. WO2010/038690.

Comparative Example 1

75 g of mirabegron, 38.79 g of polyethylene oxide (made by Dow Chemical, WSR-301, having an average molecular weight of 4,000,000), 45 g of polyethylene glycol (made by Sanyo Chemical, PEG 6000, hereinafter the same), 133.71 g of lactose monohydrate (made by DFE Pharma, hereinafter the same), 0.15 g of butylhydroxytoluene and 2.85 g of magnesium stearate were mixed, compacted using a mini roller compacter, and screened, thus obtaining granules. The granules thus obtained were mixed with 45 g of pulverized PROSOLV HD90 (made by JRS Pharma, silicified high-density microcrystalline cellulose composed of microcrystalline cellulose and colloidal silicon dioxide, hereinafter the same) and 7.5 g of magnesium stearate, and tableted using a rotary tableting machine, thus obtaining a tablet (232 mg per tablet). Using a coating machine, the tablet thus obtained was spray-coated with a dispersion solution of a film-coating agent (Opadry) in water, thereby yielding a coated tablet (240 mg per tablet).

Comparative Example 2

75 g of mirabegron, 44.925 g of polyethylene oxide (made by Dow Chemical, WSR-301), 45 g of polyethylene glycol, 127.575 g of lactose monohydrate, 0.15 g of butylhydroxytoluene and 2.85 g of magnesium stearate were mixed, compacted using a mini roller compacter, and screened, thus obtaining granules. The granules thus obtained were mixed with 45 g of pulverized PROSOLV HD90 and 7.5 g of magnesium stearate and tableted using a rotary tableting machine, thus obtaining a tablet (232 mg per tablet). Using a coating machine, the tablet thus obtained was spray-coated with a dispersion solution of a film-coating agent (Opadry) in water, thereby yielding a coated tablet (240 mg per tablet).

Comparative Example 3

75 g of mirabegron, 44.925 g of polyethylene oxide (made by Dow Chemical, WSR-301), 45 g of polyethylene glycol, 172.575 g of anhydrous lactose (made by DFE Pharma, hereinafter the same), 0.15 g of butylhydroxytoluene and 2.85 g of magnesium stearate were mixed, compacted using a mini roller compacter, and screened, thus obtaining granules. The granules thus obtained were mixed with 7.5 g of pulverized magnesium stearate and tableted using a rotary tableting machine, thus obtaining a tablet (232 mg per tablet). Using a coating machine, the tablet thus obtained was spray-coated with a dispersion solution of a film-coating agent (Opadry) in water, thereby yielding a coated tablet (240 mg per tablet).

Comparative Example 4

75 g of mirabegron, 45 g of polyethylene oxide (made by Dow Chemical, WSR-301), 45 g of polyethylene glycol, 127.65 g of lactose monohydrate, 45 g of PROSOLV HD90, 1.5 g of butylhydroxytoluene and 2.85 g of magnesium stearate were mixed, compacted using a mini roller compacter, and screened, thus obtaining granules. The granules thus obtained were mixed with 7.5 g of pulverized magnesium stearate and tableted using a rotary tableting machine, thus obtaining a tablet (233 mg per tablet). Using a coating machine, the tablet thus obtained was spray-coated with a dispersion solution of a film-coating agent (Opadry) in ethanol, thereby yielding a coated tablet (241 mg per tablet).

Comparative Example 5

75 g of mirabegron, 135 g of polyethylene oxide (made by Dow Chemical, WSR N-60K, having an average molecular weight of 2,000,000), 75 g of polyethylene glycol, 15 g of hydroxypropyl cellulose, 1.5 g of butylhydroxytoluene and 2.85 g of magnesium stearate were mixed, compacted using a mini roller compacter, and screened, thus obtaining granules. The granules thus obtained were mixed with 7.5 g of pulverized magnesium stearate and tableted using a rotary tableting machine, thus obtaining a tablet (207.9 mg per tablet). Using a coating machine, the tablet thus obtained was spray-coated with a dispersion solution of a film-coating agent (Opadry) in ethanol, thereby yielding a coated tablet (215.9 mg per tablet).

Respective recipes of Comparative Examples 1 to 5 are shown in Table 2 below.

Comparative Example 8

50 g of mirabegron, 140 g of polyethylene oxide (made by Dow Chemical, WSR N-60K, having an average molecular weight of 2,000,000), and 289.2 g of polyethylene glycol (PEG 6000) were placed in a fluidized-bed granulator (GPCG2, Glatt) and granulated in the presence of 150 g of a 10 wt % hydroxypropyl cellulose (HPC-L) aqueous solution, thus obtaining granules. The granules thus obtained were screened, mixed with 5 g of pulverized magnesium stearate and 0.8 g of butylhydroxytoluene (BHT), and tableted using a rotary tableting machine, thus obtaining a tablet (250 mg per tablet). Using a coating machine, the tablet thus obtained was spray-coated with a dispersion solution of a film-coating agent (Opadry) in water, thereby yielding a coated tablet (257.5 mg per tablet).

<Experimental Example 1> Related Substance Test

Related substances, particularly, other individual related substances of Comparative Examples 1 to 5 and Examples

TABLE 2

| Comparative Example | Comparative Example 1 | Comparative Example 2 | Comparative Example 3 | Comparative Example 4 | Comparative Example 5 |
|---|---|---|---|---|---|
| Mirabegron (g) | 75 | 75 | 75 | 75 | 75 |
| Polyethylene oxide (WSR N-60K, g) | — | — | — | — | 135 |
| Polyethylene oxide (WSR-301, g) | 38.79 | 44.925 | 44.925 | 45 | — |
| PEG 6000(g) | 45 | 45 | 45 | 45 | 75 |
| Lactose monohydrate (g) | 133.71 | 127.575 | — | 127.65 | — |
| Anhydrous lactose (g) | — | — | 172.575 | — | — |
| PROSOLV HD90 (g) | — | — | — | 45 | — |
| HPC-L (g) | — | — | — | — | 15 |
| Butylhydroxytoluene (g) | 0.15 | 0.15 | 0.15 | 1.5 | 1.5 |
| Magnesium stearate (g) | 2.85 | 2.85 | 2.85 | 2.85 | 2.85 |
| PROSOLV HD90 (g) | 45 | 45 | — | — | — |
| Magnesium stearate (g) | 7.5 | 7.5 | 7.5 | 7.5 | 7.5 |
| Film-coating agent (g) | Appropriate amount | Appropriate amount | Appropriate amount | Appropriate amount | Appropriate amount |

Comparative Example 6

A commercially available mirabegron preparation (Betmiga PR (prolonged-release) tab 50 mg, Lot number: 16C20/41, available from Astellas) was provided.

Comparative Example 7

75 g of mirabegron, 36.68 g of polyethylene oxide WSR N-80, 110.05 g of polyethylene oxide WSR-1105, and 78.26 g of polyethylene glycol PEG 6000 were mixed, placed in a high-speed mixer, added with a solution of 7.5 g of hydroxypropyl cellulose (HPC-L) and 1.5 g of butylhydroxytoluene (BHT) dissolved in ethanol, mixed and granulated, thus obtaining granules. The granules thus obtained were dried, screened, mixed with 7.5 g of pulverized magnesium stearate and 7.5 g of light anhydrous silicic acid (Aerosil 200), and tableted using a rotary tableting machine, thus obtaining a tablet (216 mg per tablet). Using a coating machine, the tablet thus obtained was spray-coated with a dispersion solution of a film-coating agent (Opadry) in ethanol, thereby yielding a pharmaceutical preparation (coated tablet, 224 mg per tablet).

1 and 5, were analyzed, and the amounts of impurities that were generated were evaluated. Here, the other individual related substances indicate related substances, except (R)-2-((4-aminophenethyl)amino)-1-phenylethanol {MIR-1}, 2-(2-aminothiazol-4-yl)-N-(4-(2(phenethylamino)ethyl)phenyl)acetamide {MIR deshydroxy}, (R)-2-(2-aminothiazol-4-yl)-N-(4-(2-((4-(2-((2-hydroxy-2-phenylethyl)amino)ethyl)phenyl)amino)-2-oxoethyl)thiazol-2-yl)acetamide {Diamide-2}, and (R)-2-(2-aminothiazol-4-yl)-N-(4-(2-(2-aminothiazol-4-yl)acetamido)phenethyl)-N-(2-hydroxy-2-phenylethyl)acetamide {Diamide-1}, among total related substances. The evaluation thereof was performed through high-performance liquid chromatography (HPLC), among the general test methods set forth in the Korean Pharmacopoeia. Content of MIR-1 of 0.4% or less, MIR deshydroxy of 0.4% or less, Diamide-2 of 0.4% or less, Diamide-1 of 0.4% or less, other individual related substances of 0.2% or less, and total related substances of 1.8% or less is judged as appropriate, and exceeding the above ranges is judged as inappropriate.

The specific test methods are described below.

(1) Formulation of Test Solution

A test solution for each of Comparative Example 1 to 5, Example 1 and Example 5 was formulated. Five tablets were placed in a 200 mL volumetric flask, added with 120 mL of water and stirred until the tablets were completely disintegrated, added with 80 mL of acetonitrile and stirred for 20 min, ultrasonically extracted for 10 min, cooled to room temperature, and added with a diluted solution up to the marked line. The resulting solution was centrifuged, after which exactly 15 mL of the clean supernatant was taken, placed in a 25 mL volumetric flask and then added with a diluted solution up to the marked line. An appropriate amount of the resulting solution was filtered using a membrane filter {0.45 μm}, and the first 2 mL thereof was discarded and the remaining filtrate was placed in a vial and used as a test solution. The diluted solution was a mixed solution of water and acetonitrile {water/acetonitrile (3/2)}.

(2) Formulation of Standard Solution

About 15.0 mg of mirabegron standard was precisely weighed, placed in a 100 mL volumetric flask, added with 40 mL of a diluted solution, ultrasonically extracted for 5 min and thus completely dissolved, cooled to room temperature, and added with a diluted solution up to the marked line. Exactly 1 mL of the resulting solution was taken, placed in a 100 mL volumetric flask, added with a diluted solution up to the marked line, and then filtered with a membrane filter {0.45 μm}, and the resulting filtrate was placed in a vial and thus used as a standard solution. The diluted solution was a mixed solution of water and acetonitrile {water/acetonitrile (3/2)}.

(3) Operation Conditions

Specific HPLC operation conditions were described below. The amount of related substance was calculated from peak areas $A_T$ and $A_S$ of the test solution and the standard solution.

Detector: UV Absorbance Spectrophotometer (measurement wavelength: 240 nm)

Column: XTerra RP8 (4.6 mm×250 mm, 5 μm) or column equivalent thereto

Column temperature: 27° C.
Sample temperature: 10° C.
Injected amount: 10 μL
Mobile phase: The mixing ratio of mobile phase A and mobile phase B was changed as below and controlled in a concentration gradient manner.

Mobile phase A: Buffer solution (1.56 g of sodium dihydrogen phosphate dihydrate and 0.34 g of tetrabutylammonium hydrogen sulfate were dissolved in 1000 mL of water, and the pH thereof was adjusted to 7.2 using a 5 mol/L sodium hydroxide aqueous solution)

Mobile phase B: Mixed solution of acetonitrile and water {acetonitrile/water (3/2)}

TABLE 3

| Time (min) | Flow rate (mL/min) | Mobile phase A (vol %) | Mobile phase B (vol %) |
|---|---|---|---|
| 0 | 0.8 | 75 | 25 |
| 5 | 0.8 | 75 | 25 |
| 45 | 0.8 | 20 | 80 |
| 50 | 0.8 | 0 | 100 |
| 55 | 1.5 | 75 | 25 |
| 63 | 1.5 | 75 | 25 |
| 65 | 0.8 | 75 | 25 |
| 70 | 0.8 | 75 | 25 |

(4) Calculation Equation $$\text{Amount of related substance (\%)} = \frac{W_S \times A_T \times 333 \times P}{N \times A_S \times D \times 10000 \times RRF}$$

Ws: amount of mirabegron standard that was taken (mg)
N: number of samples
$A_T$: peak area of each related substance in test solution
$A_S$: peak area of mirabegron in standard solution
D: labeled amount of mirabegron per tablet (mg)
P: purity of mirabegron standard (%)
333/10000: dilution factor
RRF: relative response factor of related substance (5) Relative Retention Time and Relative Response Factor

TABLE 4

| Material | Relative retention time (RRT) | Relative response factor (RRF) |
|---|---|---|
| MIR-1* | 0.49 | 0.80 |
| Mirabegron | 1.00 | — |
| MIR deshydroxy* | 1.11 | 0.94 |
| Diamide-2* | 1.44 | 0.67 |
| Diamide-1* | 1.68 | 0.78 |
| Other individual related substances | — | 1.00 |

In Examples, the amounts of all of MIR-1, MIR deshydroxy, Diamide-2, and Diamide-1 were evaluated to be appropriate, and the results of other individual related substances are shown for comparison with Comparative Examples in Table 5 below.

TABLE 5

| | Related substances | Uncoated tablet impurities (%) | | Coated tablet impurities (%) | |
|---|---|---|---|---|---|
| Comparative Example 1 | Other individual related substances | — | — | 1.30 | Inappropriate |
| Comparative Example 2 | Other individual related substances | 0.22 | Inappropriate | 0.97 | Inappropriate |
| Comparative Example 3 | Other individual related substances | 0.24 | Inappropriate | 0.83 | Inappropriate |
| Comparative Example 4 | Other individual related substances | 0.30 | Inappropriate | 0.37 | Inappropriate |
| Comparative Example 5 | Other individual related substances | 0.74 | Inappropriate | 0.75 | Inappropriate |

TABLE 5-continued

| Related substances | | Uncoated tablet impurities (%) | | Coated tablet impurities (%) | |
|---|---|---|---|---|---|
| Example 1 | Other individual related substances | 0.02 | Appropriate | — | — |
| Example 5 | Other individual related substances | 0.04 | Appropriate | 0.03 | Appropriate |

As is apparent from Table 5, in Comparative Examples 1 to 5, the amounts of other individual related substances exceeded 0.2% and thus were evaluated to be inappropriate. All of the preparations of Comparative Examples 1 to 5 included, as the release-controlling agent, at least one hydrophilic base that enables water to penetrate into the preparation. Among these, Comparative Examples 1 to 3 are preparations spray-coated with the water dispersion solution in the same manner as the method disclosed in International Patent Application Publication No. WO2010/038690 and Comparative Example 4 is the preparation spray-coated with the ethanol dispersion solution. Comparative Example 5 is a preparation in which the amount of polyethylene glycol in the hydrophilic base is very high compared to the other preparations.

When comparing Comparative Examples 1 to 3 with Comparative Example 4, the amounts of other individual related substances were significantly increased after coating compared to before coating. Based on these results, when spray coating was performed using the dispersion solution of the film-coating agent in ethanol, the generation of impurities was suppressed more than when using the water dispersion solution.

In Comparative Example 5, the amount of polyethylene glycol in the hydrophilic base was very high compared to the other preparations, and the amounts of other individual related substances were also high in the uncoated tablet. This shows that in many examples disclosed in International Patent Application Publication No. WO2010/038690, polyethylene glycol, serving as the hydrophilic base, may cause problems of low preparation stability.

Unlike Comparative Examples using the hydrophilic base as the release-controlling agent, in all of Examples using the release-controlling agent composed of the hydrogel-forming polymer alone, the generation of impurities was greatly suppressed, thus ensuring stability. The pharmaceutical preparation of the present invention was more stable despite the use of the release-controlling agent including the hydrogel-forming polymer alone without the hydrophilic base.

Therefore, it can be concluded that the pharmaceutical preparation of the present invention is capable of suppressing the generation of impurities and thus higher stability thereof can be obtained by using the release-controlling agent composed exclusively of the hydrogel-forming polymer (not including the hydrophilic base) and by virtue of the coating layer formed using the volatile solvent.

<Experimental Example 2> Dissolution Test

Examples and Comparative Example were subjected to a dissolution test in accordance with USP Dissolution Test Method (Paddle method). As the test solution, a pH 4.0 acetic acid buffer solution and a pH 6.8 phosphoric acid buffer solution were used in amounts of 900 mL each. Here, stirring was performed at 50 rpm. Respective results thereof are shown in Tables 6 and 7 below.

TABLE 6

| pH 4.0 | Comparative Example 1 | Example 2 | Example 3 | Example 5 |
|---|---|---|---|---|
| 1 hr | 20% | 10% | 12% | 14% |
| 3 hr | 51% | 31% | 43% | 43% |
| 8.5 hr | 97% | 88% | 91% | 97% |
| 12 hr | 99% | 95% | 91% | 98% |

TABLE 7

| pH 6.8 | Comparative Example 1 | Example 2 | Example 3 | Example 5 |
|---|---|---|---|---|
| 1 hr | 11% | 5% | 7% | 7% |
| 3 hr | 37% | 22% | 33% | 26% |
| 8.5 hr | 98% | 79% | 89% | 87% |
| 12 hr | 100% | 96% | 89% | 97% |

As is apparent from Tables 6 and 7, the dissolution rate for 1 hr was less than 20% in all of Examples. In contrast, the composition of Comparative Example exhibited the high dissolution rate.

<Experimental Example 3> Comparative Dissolution Test

Example 5 and Comparative Example 6 (Betmiga PR tab) were subjected to a dissolution test as in Experimental Example 2, and dissolution patterns were compared. The results thereof are shown in Tables 8 and 9 below and in FIGS. 2 and 3.

TABLE 8

| pH 4.0 | Average dissolution rate | | | | | | |
|---|---|---|---|---|---|---|---|
| Time (hr) | 1 | 3 | 5 | 7 | 8.5 | 10 | 12 |
| Example 5 | 14% | 43% | 73% | 93% | 97% | 97% | 98% |
| Comparative Example 6 | 13% | 41% | 69% | 90% | 97% | 97% | 96% |
| | Average dissolution rate variation (Example 5 - Comparative Example 6) | | | | | | |
| Variation | 1% | 2% | 3% | 3% | 0% | 0% | 1% |

TABLE 9

| pH 6.8 | Average dissolution rate | | | | | | |
|---|---|---|---|---|---|---|---|
| Time (hr) | 1 | 3 | 5 | 7 | 8.5 | 10 | 12 |
| Example 5 | 7% | 26% | 52% | 74% | 87% | 93% | 97% |
| Comparative Example 6 | 9% | 32% | 58% | 80% | 92% | 99% | 98% |
| Average dissolution rate variation (Example 5 - Comparative Example 6) | | | | | | | |
| Variation | −2% | −6% | −6% | −6% | −5% | −5% | −1% |

Figure 2:
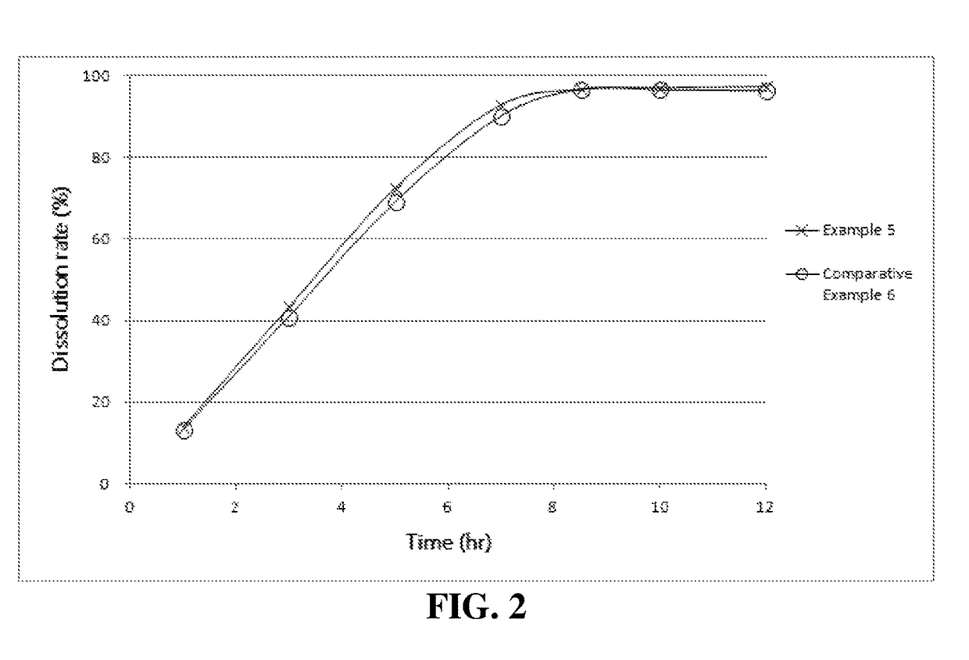
FIG. 2 is a graph showing the results of a comparative dissolution test in a pH 4.0 dissolution medium.
Figure 3:
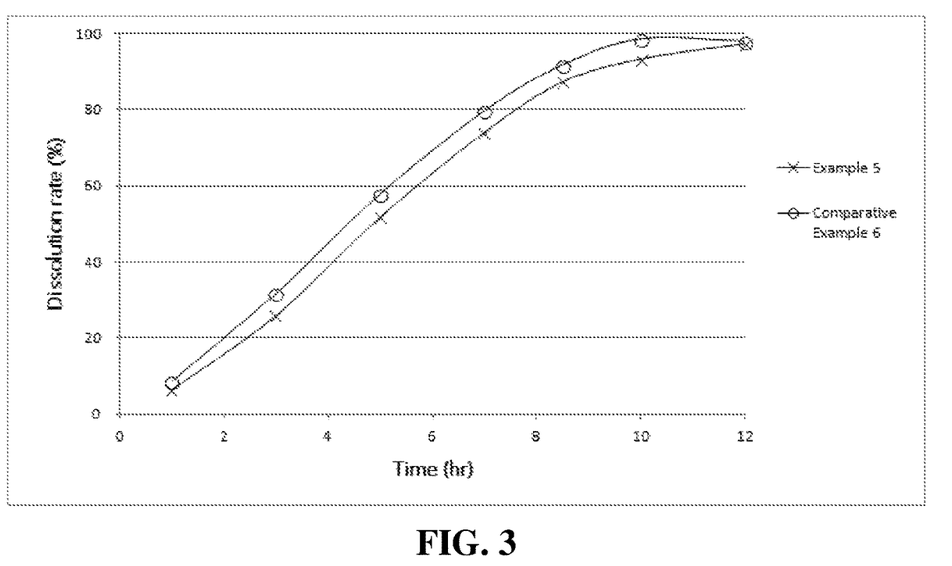
FIG. 3 is a graph showing the results of a comparative dissolution test in a pH 6.8 dissolution medium.

FIG. 2 is a graph showing the results of a comparative dissolution test in the pH 4.0 dissolution medium, and FIG. 3 is a graph showing the results of a comparative dissolution test in the pH 6.8 dissolution medium.

As is apparent from Tables 8 and 9 and FIGS. 2 and 3, the preparation of Example exhibited a dissolution pattern equivalent to that of the commercially available preparation.

Therefore, it can be concluded that the pharmaceutical preparation of the present invention can exhibit a dissolution pattern equivalent to that of a commercially available preparation, and thus pharmacokinetics equivalent thereto, and ultimately medicinal effects equivalent or superior thereto.

<Experimental Example 4> Related Substance Test for Comparative Examples 7 and 8

Related substance testing was additionally performed in the same manner as in Experimental Example 1, with the exception that Comparative Examples 7 and 8 were used, in lieu of Comparative Examples 1 to 5. The results thereof are shown in Table 10 below.

TABLE 10

| | Related substances | Uncoated tablet impurities (%) | | Coated tablet impurities (%) | |
|---|---|---|---|---|---|
| Comparative Example 7 | Other individual related substances | 0.34 | Inappropriate | 0.30 | Inappropriate |
| Comparative Example 8 | Other individual related substances | 0.34 | Inappropriate | 0.42 | Inappropriate |

As is apparent from Table 10, in Comparative Examples 7 and 8, the amounts of other individual related substances exceeded 0.2%, which is considered inappropriate. In Comparative Example 7, unlike the other Comparative Examples, two kinds of polyethylene oxides having different molecular weights were used as in Examples 3 to 5. In this case, it can be confirmed that the impurities were generated at a predetermined level or more, as in the other Comparative Examples. These results show that there is a difference in the generation of impurities depending on whether the hydrophilic base is used as the release-controlling agent. Also, Comparative Example 8 is a preparation manufactured so as to more closely match the examples disclosed in International Patent Application Publication No. WO2010/038690, compared to the other Comparative Examples. In this case, it can be confirmed that the impurities were generated at a predetermined level or more, as in the other Comparative Examples. These results show that the stability of the preparation may become problematic when using the hydrophilic base as the release-controlling agent. Therefore, based on the results of testing for related substances in Comparative Examples 7 and 8, it is further confirmed that the generation of impurities in the present invention was suppressed.

INDUSTRIAL APPLICABILITY

The pharmaceutical preparation of the present invention is capable of suppressing the generation of impurities therein and of effectively controlling the release of at least one selected from among mirabegron and a pharmaceutically acceptable salt thereof, and is thus industrially applicable.

The invention claimed is:
1. A pharmaceutical preparation, comprising:
an active ingredient and a release-controlling agent for controlling release of the active ingredient, and further comprising:
a binder, an antioxidant, a lubricant, and a coating layer,
wherein the active ingredient is at least one selected from among mirabegron and a pharmaceutically acceptable salt thereof,
the release-controlling agent consists of a hydrogel-forming polymer,
the hydrogel-forming polymer is at least one selected from among polyethylene oxide, hydroxypropyl methyl cellulose, hydroxypropyl cellulose, sodium carboxymethylcellulose, and hydroxyethyl cellulose, and has an average molecular weight ranging from 100,000 to 8,000,000,
the binder is at least one selected from among hydroxypropyl cellulose, hydroxypropyl methyl cellulose, polyvinyl pyrrolidone, methyl cellulose, carboxymethyl cellulose, sodium carboxymethylcellulose, trehalose, and pullulan,
the antioxidant is at least one selected from among butylhydroxytoluene, propyl gallate, butylhydroxyanisole, ascorbic acid, sodium ascorbate, erythorbic acid, sodium nitrite, sodium bisulfate, sodium pyrosulfite, citric acid and sodium edetate,
the lubricant is at least one selected from among magnesium stearate, calcium stearate, silicon dioxide, and talc,
the coating layer comprises a film of a coating agent dissolved or dispersed in ethanol and the coating layer is formed on a surface of a core prepared from the active ingredient, the release-controlling agent, the binder, the antioxidant, and the lubricant, and
the active ingredient is contained in an amount of 5 to 25 wt %, the release-controlling agent is contained in an amount of 60 to 90 wt %, the binder is contained in an amount of 1 to 5 wt %, the antioxidant is contained in an amount of 0.1 to 1 wt %, the lubricant is contained in an amount of 1 to 6 wt %, and the coating agent is contained in an amount of 1 to 10 wt % based on the total weight of the pharmaceutical preparation, wherein an amount of impurities is 0.2 wt % or less.

2. The pharmaceutical preparation of claim 1, wherein the lubricant comprises silicon dioxide and magnesium stearate, and an amount of the silicon dioxide is 1 to 3 wt % and an amount of the magnesium stearate is 1 to 3 wt % in the pharmaceutical preparation.

3. The pharmaceutical preparation of claim 2, wherein the silicon dioxide is colloidal silicon dioxide.

4. The pharmaceutical preparation of claim 1, wherein the coating agent is a film-coating agent.

5. The pharmaceutical preparation of claim 1, wherein the hydrogel forming polymer is polyethylene oxide, and the polyethylene oxide comprises polyethylene oxide having an average molecular weight ranging from 100,000 to less than 500,000 and polyethylene oxide having an average molecular weight ranging from 500,000 to less than 1,000,000.

6. The pharmaceutical preparation of claim 1, wherein the hydrogel-forming polymer is polyethylene oxide and has an average molecular weight ranging from 100,000 to less than 1,000,000.

7. A method of manufacturing a pharmaceutical preparation, the method comprising:
(A) manufacturing a granule by dispersing or dissolving a binder and an antioxidant in a solvent to afford a solution, which is then mixed with a mixture of an active ingredient and a release-controlling agent;
(B) obtaining a tablet by adding the granule with a lubricant and performing tableting; and
(C) coating the tablet with a film by dissolving or dispersing a film-coating agent in ethanol,
wherein the binder is hydroxypropyl cellulose,
the antioxidant is butylhydroxytoluene,
the active ingredient is at least one selected from among mirabegron and a pharmaceutically acceptable salt thereof,
the release-controlling agent consists of a hydrogel-forming polymer,
the hydrogel-forming polymer being at least one selected from among polyethylene oxide, hydroxypropyl methyl cellulose, hydroxypropyl cellulose, sodium carboxymethylcellulose, and hydroxyethyl cellulose, and having an average molecular weight ranging from 100,000 to 8,000,000,
the lubricant comprises silicon dioxide and magnesium stearate, and
the active ingredient is contained in an amount of 5 to 25 wt %, the release-controlling agent is contained in an amount of 60 to 90 wt %, the binder is contained in an amount of 1 to 5 wt %, the antioxidant is contained in an amount of 0.1 to 1 wt %, the lubricant is contained in an amount of 1 to 6 wt %, and the coating agent is contained in an amount of 1 to 10 wt % based on the total weight of the pharmaceutical preparation, wherein an amount of impurities is 0.2 wt % or less.

* * * * *